US006858608B2

(12) United States Patent
Mailliet et al.

(10) Patent No.: US 6,858,608 B2
(45) Date of Patent: Feb. 22, 2005

(54) CHEMICAL DERIVATIVES AND THEIR APPLICATION AS ANTITELOMERASE AGENTS

(75) Inventors: Patrick Mailliet, Fontenay Sous Bois (FR); Jean-François Riou, Reims (FR); Marcel Alasia, Choisy Le Roi (FR); Thomas Caulfield, Paris (FR); Gilles Doerflinger, Les Ulis (FR); Jean-Louis Mergny, Villejuif (FR); Abdelazize Laoui, Bridgewater, NJ (US); Odile Petitgenet, Paris (FR); Emmanuelle Renou, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/040,370

(22) Filed: Jan. 9, 2002

(65) Prior Publication Data

US 2003/0078263 A1 Apr. 24, 2003

Related U.S. Application Data

(60) Provisional application No. 60/270,164, filed on Feb. 22, 2001.

(30) Foreign Application Priority Data

Jan. 9, 2001 (FR) ............................................. 01 00205

(51) Int. Cl.$^7$ ..................... C07D 213/02; C07D 215/38; C07D 251/48; A61K 31/53; A61P 35/00
(52) U.S. Cl. ........................ 514/241; 544/196; 544/198; 544/205; 544/206; 544/207; 544/208; 544/209
(58) Field of Search ................................. 544/196, 197, 544/198, 205, 206, 207, 208, 209; 514/241, 248

(56) References Cited

U.S. PATENT DOCUMENTS 5,767,278 A 6/1998 Gaeta .......................... 546/261
6,150,360 A * 11/2000 Daeyaert et al. ............ 544/194

FOREIGN PATENT DOCUMENTS

JP 11060573 3/1999
WO WO 93/20056 10/1993

* cited by examiner

Primary Examiner—Venkataraman Balasubramanian
(74) Attorney, Agent, or Firm—Balaram Gupta

(57) ABSTRACT

The present invention relates to cancer therapy and to novel anticancer agents having a mechanism of action which inhibits telomerase. It also relates to novel chemical compounds as well as their therapeutic application in humans.

30 Claims, No Drawings

CHEMICAL DERIVATIVES AND THEIR APPLICATION AS ANTITELOMERASE AGENTS

This application claims the benefit of priority from French Application No. 0100205, filed Jan. 9, 2001, and U.S. Provisional Application No. 60/270,164, filed Feb. 22, 2001, which are both incorporated herein by reference in their entirety.

The present invention relates to cancer therapy and to novel anticancer agents having a mechanism of action which is quite specific. It also relates to novel chemical compounds as well as their therapeutic application in humans.

The present invention relates to the use of novel non-nucleotide chemical compounds which interact with specific structures of deoxyribonucleic acid (DNA). These novel compounds consist of a distribution agent linked to an aminoaromatic group. These novel compounds are useful in the treatment of cancers and typically act as telomerase-inhibiting agents. They are also useful for stabilizing DNA in G-quadruplex structures (e.g., guanine tetrads). The inhibition of telomerase via the stabilization of these G-quadruplexes generally results in the termination of cellular mitosis and the death of rapidly-dividing cells such as cancer cells. It may also result in the induction of senescence in cancer cells. Thus, such telomerase inhibiting agents have important therapeutic applications.

The compounds of the present invention have the advantage, from the therapeutic point of view, of blocking telomerase. From a biological point of view, telomerase allows the addition of repetitive DNA sequences of the T T A G G G type (termed telomeric sequences) to the end of the telomere during cell division. Through this action, telomerase renders the cell immortal. Indeed, in the absence of this enzymatic activity, the cell loses 100 to 150 bases at each division, which rapidly renders it senescent. During the development of rapidly-dividing cancer cells, these cells were found to possess telomeres which were maintained at a stable length during cell division. In these cancer cells, telomerase was found to be highly activated and allowed the addition of repetitive motifs of telomeric sequences at the end of the telomere. This allowed conservation of the length of the telomeres in the cancer cells. During the past few years, more than 85% of cancer cells have tested positive for the presence of telomerase, whereas somatic cells do not show this characteristic.

Thus, telomerase is an important target for treating cancer cells. The first approach for blocking telomerase was the use of nucleotide structures (Chen et al., Proc. Natl. Acad. Sci. USA 93(7), 2635–2639). Diaminoanthraquinones (Sun et al., J. Med. Chem. 40(14), 2113–6) and diethyloxadicarbo-cyanins (Wheelhouse R. T. et al., J. Am. Chem. Soc. 120:3261–2, 1998) are among the non-nucleotide compounds which have been used.

Patent WO 99/40087 describes the use of compounds which interact with the G-quadruplex structures. Such G-quadruplex structures are typically perylene compounds and carbocyanins containing at least seven rings, including two heterocycles.

It has been discovered, quite surprisingly, that simple structures could achieve a result which is at least equivalent with structures which are a lot less complicated from a chemical point of view. The compounds of the present invention which meet the intended objective, i.e., which bind the G-quadruplex structure and thereby exhibit a telomerase-inhibiting activity, correspond to the following general formula:

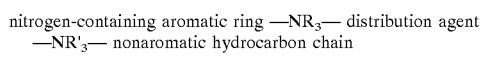

nitrogen-containing aromatic ring —NR$_3$— distribution agent —NR'$_3$— nonaromatic hydrocarbon chain in which the nitrogen-containing aromatic ring represents:
  a quinoline optionally substituted with at least
    a group N(Ra)(Rb) in which Ra and Rb, which are identical or different, represent hydrogen or a C1–C4 alkyl radical or
    a group ORa in which Ra is as defined above
  a quinoline possessing a nitrogen atom in quaternary form or
  a benzamidine or
  a pyridine
R3 and R'3, which are identical or different, represent independently of each other hydrogen or a C1–C4 alkyl radical
the distribution agent represents:
  a triazine group optionally substituted with an alkyl radical having 1 to 4 carbon atoms, a thio, oxy or amino radical which are themselves optionally substituted with one or more short-chain alkyl chains containing 1 to 4 carbon atoms or alternatively a halogen atom or
  a carbonyl group or
  a group C(=NH)—NH—C(=NH) or
  an alkyldiyl group containing 3 to 7 carbon atoms or
  a diazine group optionally substituted with the same groups as triazine or one of its salts.

For the purposes of the above formula, nonaromatic hydrocarbon chain is understood to mean an alkyl (C1–C4) or alkenyl (C2–C4) chain, which is linear or branched, or a cycloalkyl (C3–C18), cycloalkenyl (C3–C18) or heterocycloalkyl (C3–C18) chain. The heterocycloalkyl group optionally includes the nitrogen atom.

It is of course understood that the nonaromatic hydrocarbon chain may be optionally substituted with one or more atoms or radicals chosen from among halogen atoms, hydroxyl, aryl, heteroaryl, alkyloxy, aryloxy, thio, alkylthio, arylthio, amino, alkylamino and/or arylamino, dialkylamino, diarylamino, amidino, guanidino, alkylcarbonylamino, arylcarbonylamino, carboxyl, alkyloxycarbonyl, aryloxycarbonyl, aminocarbonyl, alkylaminocarbonyl, arylaminocarbonyl, dialkylaminocarbonyl, alkylcarbonyl, arylcarbonyl, cyano, trifluoromethyl, and combinations thereof.

The alkyl chains of the optional substituents of the hydrocarbon chain may contain 1 to 4 carbon atoms; and the aryl groups of the optional substituents of the hydrocarbon chain may contain 5 to 18 carbon atoms.

In one embodiment, the compounds include a distribution agent chosen from a triazine and a diazine group. Suitable diazine groups include pyrimidines and quinazolines. The hydrocarbon chains may be alkyl chains containing 2 to 3 carbon atoms; and the heterocycloalkyl or cycloalkyl chains may contain 4 to 7 carbon atoms.

Suitable triazines include the compounds corresponding to formula (I) below:

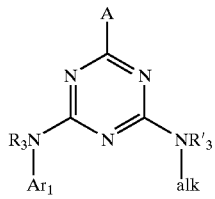

in which:

A represents
an amino group of formula NR1R2 in which R1 and R2, which are identical or different, represent hydrogen or a straight or branched alkyl group containing 1 to 4 carbon atoms or
a group OR1 or SR1 in which R1 has the same meaning as above or
an alkyl group containing 1 to 4 carbon atoms or a trifluoromethyl group or
a hydrogen atom or
a halogen atom chosen from fluorine, chlorine, bromine, and iodine $R_3$ and $R'_3$, which are identical or different, represent independently of each other hydrogen or a C1–C4 alkyl radical, $Ar_1$ represents:
a nitrogen-containing aromatic ring representing:
a quinoline optionally substituted with at least
a group N(Ra)(Rb) in which Ra and Rb, which are identical or different, represent hydrogen or a C1–C4 alkyl radical or
a group ORa in which Ra is as defined above
a quinoline possessing a nitrogen atom in quaternary form or
a benzamidine or
a pyridine attached at the 4-position or fused with an aryl or heteroaryl group optionally substituted with a C1–C4 alkyl group alk represents
an alkyl unit containing 2 to 3 linear or branched carbon atoms substituted with an amino, alkylamino, arylamino, dialkylamino, diarylamino, or combination thereof
an alkenyl unit containing 2 to 3 carbon atoms substituted with an amino, alkylamino, arylamino, dialkylamino, diarylamino, or combination thereof
a heterocyclyl unit containing from 4 to 7 carbon atoms or one of its salts.

It is evident that the quinoline motifs may be substituted by any other group not involved in the intended application; thus, acridine, isoquinoline, quinazoline, quinoxaline, phthalazine, benzothiazine, benzoxazine, phenoxazine, and phenothiazine groups are included in the definition of the quinoline groups.

In one embodiment, compounds of formula (I) include those comprising a heterocycle chosen from the 4-aminoquinolyl, 4-alkyl- and 4-dialkyl-aminoquinolyl, 4-aminoquinolinium and quinolinium groups in which the quinolinium ring is optionally substituted with a methyl group.

Group A may represent methylthio, amino, alkylamino or dialkylamino radical, in which the alkyl groups in the radicals possess 1 to 4 carbon atoms.

The nonaromatic hydrocarbon chain may represent a 2-(dialkylamino)ethyl, 3-(dialkylamino)propyl, 2-(N-alkyl-N-arylamino)ethyl, or 3-(N-alkyl-N-arylamino)propyl chain in which the alkyl groups may contain 1 to 4 carbon atoms or, in an alternative embodiment, 1 to 2 carbon atoms; and the aryl groups may contain 5 to 18 carbon atoms or, in an alternative embodiment, 6 carbon atoms.

Another subject of the present invention relates to the compounds of formula (I) as novel chemical products. It therefore relates to the novel products corresponding to the following formula (I):

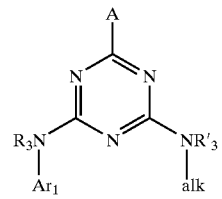

in which:

A represents
an amino group of formula NR1R2 in which R1 and R2, which are identical or different, represent a straight or branched alkyl group containing 1 to 4 carbon atoms or
a group OR1 or SR1 in which R1 represents hydrogen or has the same meaning as above or
an alkyl group containing 1 to 4 carbon atoms or a trifluoromethyl group or
a hydrogen atom or
a halogen atom chosen from fluorine, chlorine, bromine, and iodine $R_3$ and $R'_3$, which are identical or different, represent independently of each other a hydrogen atom or a C1–C4 alkyl group, $Ar_1$ represents:
a nitrogen-containing aromatic ring representing:
a quinoline optionally substituted with at least
a group N(Ra)(Rb) in which Ra and Rb, which are identical or different, represent hydrogen or a C1–C4 alkyl radical or
a group ORa in which Ra is as defined above
quinoline possessing a nitrogen atom in quaternary form or
a benzamidine or
a pyridine attached at the 4-position or fused with an aryl or heteroaryl group optionally substituted with a C1–C4 alkyl group alk represents
an alkyl unit containing 2 to 3 linear or branched carbon atoms substituted with an amino, alkylamino, arylamino, dialkylamino, diarylamino, or combination thereof
an alkenyl unit containing 2 to 3 carbon atoms substituted with an amino, alkylamino, arylamino, dialkylamino, diarylamino, or combination thereof
a heterocyclyl unit containing from 5 to 7 carbon atoms or one of its salts.

In one embodiment, $Ar_1$ represents a group chosen from among 4-amino-, 4-methylamino- and 4-dimethylamino-quinolyl and quinolynium groups, in which the quinolinium nucleus is optionally substituted with a methyl group.

The A group may represent an amino or dimethylamino or methylthio group.

The compounds of general formula (I) include those for which the nonaromatic hydrocarbon chain may represent a 2-(dialkylamino)ethyl, 3-(dialkylamino)propyl, 2-(N-alkyl-N-arylamino)ethyl or 3-(N-alkyl-N-arylamino)propyl chain in which the alkyl groups contain 1 to 4 carbon atoms, or 1 to 2 carbon atoms; and the aryl groups contain 5 to 18 carbon atoms or 6 carbon atoms.

For example, the nonaromatic hydrocarbon chain may represent a 2-(N-m.tolyl-N-ethylamino)ethyl chain.

Another subject of the present invention relates to the use of the compounds of formula (I) as pharmaceutical products for human use.

The methods of preparing the compounds of formula (I)

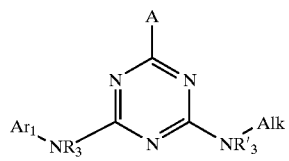

(I)

are described below.

In the case where $Ar_1$ and Alk are present, the triazine of general formula (A) may be obtained by sequential displacement of the halogen atoms, most generally of chlorine atoms, from the products of general formula (B), by the amines $Ar_1$ and then Alk of general formula (C), according to scheme 1:

It is also possible to carry out the procedure under the conditions described in J. Fluor. Chem., 1988, 39(1), 117–123, which is herein incorporated by reference.

General Method 2

According to a second method, the products of general formula (A) in which Ar are as defined above and R represents a group NR1R2 or OR1 or SR1 may also be prepared by nucleophilic displacement of a halogen atom, generally a chlorine atom, from a product of general formula (A) in which R represents a halogen atom. This second method is performed according to scheme 2:

Scheme 2

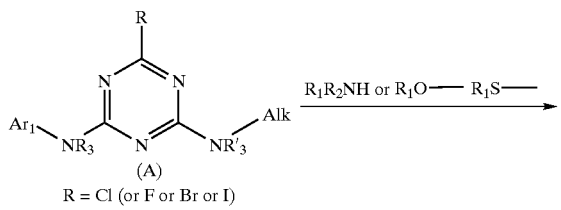

(A)

R = Cl (or F or Br or I)

Scheme 1

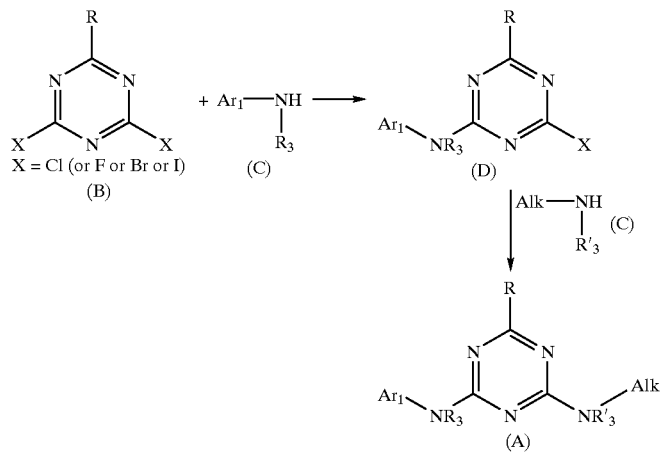

Generally, the procedure is carried out with 1 mole of dihalo-s-triazine, or trihalo-s-triazine, and 1 mole of amine $Ar_1$. The procedure is typically carried out in an inert solvent, such as acetone, which is optionally aqueous; or an alcohol which is optionally aqueous, such as ethanol; or a halogenated solvent, such as dichloromethane; or an ether, such as diethyl ether or dioxane; or a polar aprotic solvent, such as DMF, DMSO or NMP. In one embodiment, the procedure is carried out at a temperature of between 20° C. and 50° C. Next, 1 mole of amine Alk is added to the product of general formula (D), which may be optionally isolated. The procedure is generally carried out at a temperature of between 50° C. and the reflux temperature.

-continued

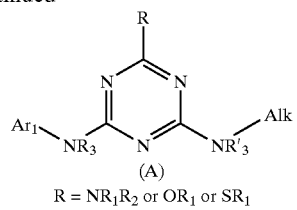

(A)

R = NR₁R₂ or OR₁ or SR₁

The procedure is generally carried out by condensing 1 mole of product of general formula (A) in which R represents a halogen atom, preferably a chlorine atom, with 1 mole of amine R1R2NH or alcoholate R1O⁻ or thioalcoholate R1S. The reaction takes place in an inert medium under the reaction conditions. There may be mentioned among the inert solvents acetone, which is optionally aqueous; or an alcohol, which is optionally aqueous such as ethanol; or a halogenated solvent, such as dichloromethane; or an ether, such as diethyl ether or dioxane; or a polar aprotic solvent, such as DMF, DMSO or NMP. When the entering group is a R1R2NH group, the procedure is typically carried out at a temperature of between 20° C. and the reflux temperature, in the presence of an organic base such as triethylamine, or an inorganic base such as sodium hydroxide or sodium or potassium carbonate. It is also possible not to use a base during the amination reaction, and to isolate a hydrochloride of the product of general formula (A), the base of which can then be released. When the entering group represents a R1O⁻ or R1S⁻ group, the procedure is typically carried out with an alkali metal or alkaline-earth metal alcoholate or thioalcoholate, such as a sodium or potassium or lithium or ammonium or cesium or barium salt, in a polar aprotic solvent such as DMF or DMSO or NMP, at a temperature of between 50° C. and the reflux temperature.

General Method 3

According to a third method of preparing the compounds, for which R represents a hydrogen atom or a straight or branched alkyl group containing from 1 to 4 carbon atoms, the compounds may be prepared by condensation of a bisguanide of general formula (E), with an acid derivative, such as an acid chloride or a methyl ester of general formula (F) according to scheme 3:

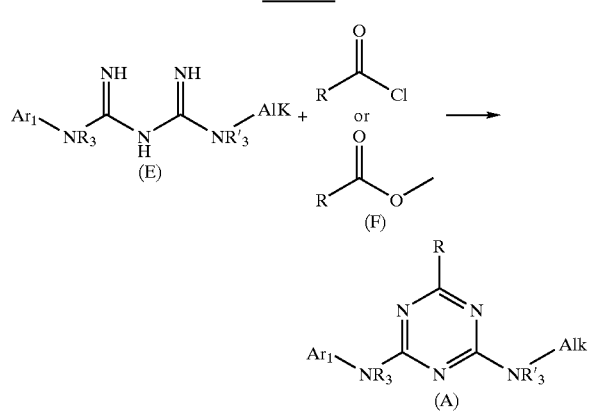

The condensation between the bisguanide of general formula (E) and the acid derivative of general formula (F) is generally carried out in an alcohol such as methanol or ethanol. The procedure is typically carried out at a temperature of between 0° C. and the reflux temperature.

The symmetric or asymmetric bisguanides of general formula (E) may be obtained by carrying out the procedure under the conditions described in the literature, for example, according to Patent J.P. 94-4993.

General Method 4

It is understood that the s-triazines, in general, may be obtained in the form of libraries, by applying the methods described in schemes 1, 2, or 3 in parallel and/or combinatorial chemistry in liquid phase or in solid phase. It is generally understood that when the work is carried out in solid phase, any one of the reagents may be attached beforehand onto a solid support, chosen according to the chemical reaction involved, and that such a chemical reaction is followed by an operation of cleaving the product of the reaction from the solid support.

The present invention also relates to therapeutic compositions containing a compound according to the invention, in combination with a pharmaceutically acceptable carrier. Such a carrier is typically chosen in accordance with the desired mode of administration. The pharmaceutical composition may be provided in solid, liquid or liposome form.

Suitable solid compositions include powders, gelatin capsules, and tablets. Among the oral forms, it is also possible to provide solid forms which are protected from the acidic medium of the stomach. The carriers used for the solid forms may comprise inorganic carriers such as phosphates, carbonates, or organic carriers such as lactose, celluloses, starch or polymers. The liquid forms may comprise solutions, suspensions or dispersions. They may also contain, as a dispersive carrier, either water, or an organic solvent (ethanol, NMP and the like), or mixtures of surfactants and solvents, or mixtures of complexing agents and solvents.

The administered dose of the compounds of the invention will be adjusted by the practitioner according to the route of administration to the patient and the condition of the patient.

The compounds of the present invention may be administered alone or mixed with other anticancer agents. Suitable agents include, but are not limited to:

alkylating agents such as cyclophosphamide, melphalan, ifosfamide, chlorambucil, busulfan, thiotepa, prednimustine, carmustine, lomustine, semustine, steptozotocin, decarbazine, temozolomide, procarbazine and hexamethylmelamine platinum derivatives such as cisplatin, carboplatin or oxaliplatin antibiotic agents such as bleomycin, mitomycin, dactinomycin, antimicrotubule agents such as vinblastine, vincristine, vindesine, vinorelbine, taxoids (paclitaxel and docetaxel)

anthracyclines such as doxorubicin, daunorubicin, idarubicin, epirubicin, mitoxantrone, losoxantrone group I and II topoisomerases such as etoposide, teniposide, amsacrine, irinotecan, topotecan and tomudex, fluoropyrimidines such as 5-fluorouracil, UFT, floxuridine, cytidine analogs such as 5-azacytidine, cytarabine, gemcitabine, 6-mercaptomurine, 6-thioguanine adenosine analogs such as pentostatin, cytarabine or fludarabine phosphate methotrexate and folinic acid enzymes and various compounds such as L-asparaginase, hydroxyurea, trans-retinoic acid, suramine, dexrazoxane, amifostine, herceptin as well as estrogenic and androgenic hormones.

It is also possible to combine a radiation treatment with the compounds of the present invention. These treatments may be administered simultaneously, separately or sequentially. The treatment is typically adapted by the practitioner to the patient to be treated.

The G-quadruplex stabilizing activity may be determined by a method using the formation of a complex with fluorescein, as described below.

Oligonucleotides

All the oligonucleotides, modified or otherwise, were synthesized by Eurogentec SA, Seraing, Belgium. The oligonucleotide FAM+DABCYL carries the catalog reference OL-0371-0802. It has the sequence: GGGTTAGGGT-TAGGGTTAGGG (SEQ ID NO:1) corresponding to 3.5 repeats of the human telomeric motif (strand rich in G). The fluorescein is chemically attached to the 5' end, and the DABCYL to the 3' end, as described by Eurogentec. The concentration of the samples is checked by spectrophotometry, recording the absorbance spectrum between 220 and 700 nm and using the molar extinction coefficient provided by the supplier.

Buffers

All the experiments were carried out in a 10 mM sodium cacodylate buffer pH 7.6 containing 0.1 M Lithium Chloride (or Sodium Chloride). The absence of fluorescent contamination in the buffer was checked beforehand. The fluorescent oligonucleotide is added at the final concentration of 0.2 µM.

Study of Fluorescence

All the measurements of fluorescence were carried out on a Spex Fluorolog DM1B apparatus, using an excitation line width of 1.8 nm and an emission line width of 4.5 nm. The samples are placed in a microquartz cuvette of 0.2×1 cm. The temperature of the sample is controlled by an external water bath. The oligonucleotide alone was analyzed at 20, 30, 40, 50, 60, 70 and 80° C. The emission spectra are recorded using an excitation wavelength of 470 nm. The excitation spectra are recorded using either 515 nm or 588 nm as emission wavelength. The spectra are corrected for the response of the instrument by reference curves. A high extinction (80–90%) of the fluorescence of fluorescein at room temperature is observed, in agreement with an intramolecular folding of the oligonucleotide at 20° C. in the form of a G-quadruplex. Such folding induces juxtaposition of the 5' and 3' ends of the oligonucleotide, which are respectively linked to fluorescein and to DABCYL. This juxtaposition causes an already-described phenomenon of extinction of fluorescence which is used for "Molecular Beacons".

Fluorescence Tm

An oligonucleotide stock solution at the strand concentration of 0.2 µM in 0.1 M LiCl, 10 mM cacodylate buffer, pH 7.6, is prepared beforehand, heated briefly at 90° C. and slowly cooled to 20° C., and then distributed in aliquots of 600 µl in the fluorescence cuvettes. Three µl of water (for the control) or 3 µl of test product (stock at 200 µM, final concentration 1 µM) are then added and mixed. The samples are then allowed to incubate for at least 1 hour at 20° C. before each measurement. The use of longer incubation times (up to 24 hours) has no influence on the result obtained.

Each experiment allows the measurement of only one sample. The latter is first incubated at an initial temperature of 20° C., heated to 80° C. over 38 minutes, left for 5 minutes at 80° C. and then cooled to 20° C. over 62 minutes. During this time, the fluorescence is measured simultaneously at two emission wavelengths (515 nm and 588 nm) using 470 nm as the excitation wavelength. A measurement is carried out every 30 seconds. The temperature of the water bath is recorded in parallel. The fluorescence profile as a function of the temperature is reconstituted from these values. The fluorescence profiles are then normalized between 20° C. and 80° C. The temperature for which the intensity of emission at 515 nm is the mean of those at high and low temperature is called the Tm. Under these conditions, the Tm of the reference sample without addition of product is 44° C. in a Lithium Chloride buffer. This temperature is increased to more than 55° C. in a Sodium Chloride buffer. The addition of a G-quadruplex stabilizing compound induces an increase in the Tm. This increase is judged to be significant if it is greater than 3°.

The antitelomerase biological activity is determined by the following experimental protocol:

Preparation of the Extract Enriched in Human Telomerase Activity

The leukemia line HL60 is obtained from ATCC (American Type Culture Collection, Rockville USA). The cells are cultured in suspension in RPMI 1640 medium containing L-Glutamine at 2 mM, Penicillin 200 U/ml, streptomycin 200 µg/ml, gentamycin 50 µg/ml and supplemented with 10% heat-inactivated fetal calf serum.

An aliquot of $10^5$ cells is centrifuged at 3000×G and the supernatant discarded. The cell pellet is resuspended by several successive pipettings in 200 µl of lysis buffer containing 0.5% CHAPS, 10 mM Tris-HCl pH 7.5, 1 mM $MgCl_2$, 1 mM EGTA, 5 mM β-mercaptoethanol, 0.1 mM PMSF and 10% glycerol and is stored in ice for 30 minutes. The lysate is centrifuged at 16 0000×G for 20 minutes at 4° C., and 160 µl of supernatant is recovered. The proteins in the extract are assayed by the Bradford method. The extract is stored at −80° C.

Assay of the Telomerase Activity

The inhibition of the telomerase activity is determined by a protocol for extension of the oligonucleotide TS ($5'$AATCGTTCGAGCAGAGTT$3'$) (SEQ ID NO:2), in the presence of a cellular extract enriched in telomerase activity and compounds which are added at various concentrations (10, 1, 0.1 and 0.01 µg/ml). The extension reaction is followed by a PCR amplification of the extension products with the aid of the oligonucleotides TS and CXext ($5'$GTGCCCTTACCCTTACCCTTACCCTAA$3'$). (SEQ ID NO:3)

The reaction medium is prepared based on the following composition:

| | |
|---|---|
| Tris HCl pH 8.3 | 20 mM |
| MgCl2 | 1.5 mM |
| Tween 20 | 0.005% (W/V) |
| EGTA | 1 mM |
| DATP | 50 µM |
| DGTP | 50 µM |
| DCTP | 50 µM |
| DTTP | 50 µM |
| Oligonucleotide TS | 2 µg/ml |
| Oligonucleotide CXext | 2 µg/ml |
| Bovine serum albumin | 0.1 mg/ml |
| Taq DNA polymerase | 1 U/ml |
| alpha 32P dCTP (3000 Ci/mmol) | 0.5 µl |
| Telomerase extract | 200 ng in a volume of 10 µl |

-continued

| Test product or solvent | in a volume of 5 μl |
| Double distilled water QS | 50 μl |

The oligonucleotides are obtained from Eurogentec (Belgium) and are stored at −20° C. at a stock concentration of 1 mg/ml in distilled water.

The reaction samples are assembled in 0.2 ml PCR tubes and one drop of paraffin oil is deposited on each of the reactions of the experiment before closing the tubes.

The reaction samples are then incubated in a Cetus 4800-type PCR apparatus under the following temperature conditions:

15 minutes at 30° C., 1 minute at 90° C., followed by 30 cycle of, 30 seconds at 94° C., 30 seconds at 50° C., and 1 minute 30 seconds at 72° C., followed by a final cycle of 2 minutes at 72° C.

For each of the samples, an aliquot of 10 μl is pipetted under the oil layer and mixed with 5 μl of a loading buffer containing:

| TBE | 3X |
| glycerol | 32% (W/V) |
| Bromophenol blue | 0.03% |
| Xylene cyanol | 0.03% |

The samples are then analyzed by electrophoresis on 12% acrylamide gel in a 1×TBE buffer for 1 hour at a voltage of 200 volts, with the aid of a Novex electrophoresis system.

The acrylamide gels are then dried on a sheet of whatmann 3MM paper at 80° C. for 1 hour.

The analysis and the quantification of the reaction products are carried out with the aid of an InstantImager apparatus (Pacard).

For each compound concentration tested, the results are expressed as percentage inhibition of the reaction and calculated from the untreated enzymatic control and from the enzyme-free sample (blank) according to the following formula:

(Compound Value−blank value/enzymatic control value−blank value)×100.

The concentration of compound inducing a 50% inhibition of the telomerase reaction (IC50) is determined with the aid of a semilogarithmic graphical representation of the inhibition values obtained as a function of each of the compound concentrations tested.

A compound is considered to be active as an antitelomerase agent when the quantity inhibiting 50% of the telomerase reaction is less than 5 μM.

The Cytotoxic Biological Activity on Human Tumor Lines is Determined According to the Following Experimental Protocol The human cell lines KB and A549 are obtained from ATCC (American Type Culture Collection, Rockville USA).

The A549 cells are cultured in a layer in a culture flask in RPMI 1640 medium containing L-Glutamine at 2 mM, Penicillin 200 U/ml, streptomycin 200 μg/ml and supplemented with 10% heat-inactivated fetal calf serum. The KB cells are cultured in a layer in a culture flask in Dulbelco's medium containing L-Glutamine at 2 mM, Penicillin 200 U/ml, streptomycin 200 μg/ml and supplemented with 10% heat-inactivated fetal calf serum.

The cells at the exponential growth phase are trypsinized, washed in 1×PBS and are inoculated in 96-well microplates (Costar) in an amount of 4×10$^4$ cells/ml for A549 and of 1.5×10$^4$ cells/ml (0.2 ml/well) and then incubated for 96 hours in the presence of variable concentrations of product to be studied (10, 1, 0.1 and 0.01 μg/ml, each point in quadruplicate). 16 hours before the end of the incubation, 0.02% final of neutral red is added to each well. At the end of the incubation, the cells are washed with 1×PBS and lysed with 1% sodium lauryl sulfate. The cellular incorporation of the dye, which reflects cellular growth, is evaluated by spectrophotometry at a wavelength of 540 nm for each sample with the aid of a Dynatech MR5000 reading apparatus.

For each compound concentration tested, the results are expressed as percentage inhibition of cellular growth and calculated from the untreated control and the culture medium free of cells (blank) according to the following formula:

(Compound Value−blank value/cell control value−blank value)×100.

The concentration of compound inducing a 50% inhibition of growth (IC50) is determined with the aid of a semilogarithmic graphical representation of the inhibition values obtained as a function of each of the compound concentrations tested.

A compound is considered to be active as cytotoxic agent if the concentration inhibiting the growth of the tumor cells tested by 50% is in particular less than 10 μM.

The following and nonlimiting examples are given to illustrate the invention.

EXAMPLE 1

Parallel Synthesis of Substituted Derivatives of N6-[6-amino-4-methylsulfanyl-[1,3,5]triazin-2-yl]-2-methylquinoline-4,6-diamine

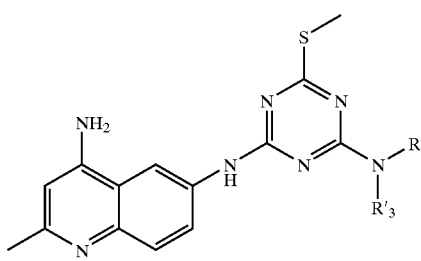

Preparation of N6-(6-chloro-4-methylsulfanyl-[1,3,5]triazin-2-yl)-2-methylquinoline-4,6-diamine 4.4 g (25 mmol) of 2-methylquinoline-4,6-diamine (which may be prepared according to J. Med. Chem., 35:252, 1992) and 2.8 g (25 mmol) of sodium carbonate are successively added, in a 1 liter three-necked flask, to a solution of 5 g (25 mmol) of 2,6-dichloro-6-methylsulfanyl-[1,3,5]triazine (which may be prepared according to J. Amer. Chem. Soc., 67:662, 1945), in 400 ml of tetrahydrofuran. The reaction mixture is heated under reflux for 16 hours. After evaporation of the tetrahydrofuran, the residue is taken up in 400 ml of a mixture of water and dichloromethane (50-50 by volume). The organic phase is separated after settling out, dried over sodium sulfate and concentrated to dryness under reduced pressure. 7.5 g (88%) of N6-(6-chloro-4-methylsulfanyl-triazin-2-yl)-2-methylquinoline-4,6-diamine are then obtained, in the form of a pale yellow solid whose characteristics are the following:

melting point=294° C.

$^1$H NMR spectrum (300 MHz, $(CD_3)_2SO$ d6, δ in ppm): 2.43 (s: 3H); 2.52 (s: 3H); 6.47 (s: 1H); 6.61 (unresolved complex: 2H); 7.62 (broad d, J=9 Hz: 1H); 7.69 (d, J=9 Hz: 1H); 8.32 (unresolved complex: 1H); 10.80 (unresolved complex: 1H).

Parallel Synthesis of N6-[6-(2-dimethylaminoethylamino)-4-methylsulfanyl-[1,3,5]triazin-2-yl]-2-methylquinoline-4,6-diamine

EXAMPLE 1-1

50 mg (0.15 mmol) of N6-(6-amino-4-methyl-sulfanyl-[1,3,5]triazin-2-yl)-2-methylquinoline-4,6-diamine are introduced into a heating magnetic reactor with a Zymark condenser, of the STEM RS2050 type, containing 25 wells in parallel each provided with a 50 ml glass tube. 5 ml of dioxane, 16 mg (0.15 mmol) of sodium carbonate, 23 mg (0.15 mmol) of sodium iodide and 27 mg (0.3 mmol) of 2-dimethylaminoethylamine are successively added to the first tube (Example 1-1). The reaction medium is heated by reflux and under argon for 24 hours. After cooling, the content of the tube is evaporated under reduced pressure, taken up in 5 ml of water and 5 ml of ethyl acetate and filtered. The organic phase is separated by settling out, dried and concentrated under reduced pressure. The crude product obtained is then purified by LC/MS using a Waters Xterra 3.5 µM C18 silica column 3 mm in diameter and 50 mm in length, eluting with a linear elution gradient consisting, at the starting time ($t_0$=0 min), of water containing 0.05% trifluoroacetic acid and, at the final time ($t_f$=4 min), of acetonitrile containing 0.05% trifluoroacetic acid. 58 mg of N6-[(6-(methylquinolin-6-ylamino)-4-methylthiotriazin-2-yl]quinaldine-4,6-diamine trifluoroacetate are thus obtained, after purification, whose characteristics are the following:

mass spectrum (DAD-TIC)=454 ($MH^+$)

retention time=2.69 min (the retention times are obtained on a hypersil C 18 5 µm column 50 mm diameter 4.6 mm trade mark Purity Elite, eluting with a mixture of solvents A (H2O/TFA 0.05%) and B (ACN/TFA 0.05%) with a linear gradient ranging from 95% A/5% B (t=0 min) to 10% A/90% B at t=3.5 min, then step 2 min).

Examples 1-1 to 1-26 were obtained by carrying out the procedure as above in a Zymark STEM RS2050 reactor. The structures, the various operating conditions used and the characteristics of Examples 1-1 to 1-26 are summarized in the table below:

| | | Reaction conditions | | | Characteristics | |
|---|---|---|---|---|---|---|
| Example | Structure AlkN(R'3- | Solvent | Heating | No. of mmol of amine | Mass $MH^+$ | Retention time (min) |
| 1-1 | | dioxane | 17 h./100° | 0.3 | 384 | 2.69 |
| 1-2 | | dioxane | 17 h./100° | 0.3 | 410 | 2.91 |
| 1-3 | trans racemic | dioxane | 17 h./100° | 0.15 | 411 | 2.86 |
| 1-4 | 3-RS | dioxane | 3 d/100° | 0.45 | 422 | 2.85 |
| 1-5 | 2-S | dioxane | 17 h./100° | 0.15 | 396 | 2.84 |

-continued

| Example | Structure AlkN(R'3- | Reaction conditions | | | Characteristics | |
|---|---|---|---|---|---|---|
| | | Solvent | Heating | No. of mmol of amine | Mass MH+ | Retention time (min) |
| 1-6 | 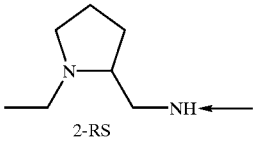<br>2-RS | dioxane | 17 h./100° | 0.15 | 424 | 2.79 |
| 1-7 | 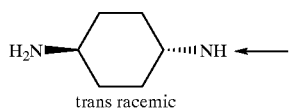<br>trans racemic | dioxane | 17 h./100° | 0.15 | 410 | 2.72 |
| 1-8 | 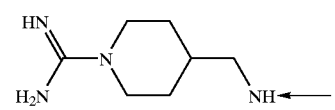 | dioxane | 2 d/100° | 0.3 | 452 | 2.81 |
| 1-9 | 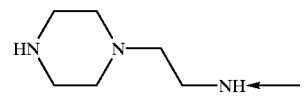 | dioxane 10 ml/DMF 1% | 24 h./100° | 0.3 | 425 | 2.43 |
| 1-10 | 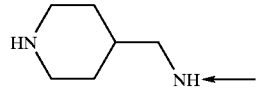 | dioxane 10 ml/DMF 1% | 24 h./100° | 0.3 | 410 | 2.51 |
| 1-11 | 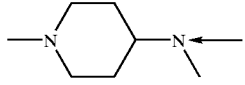 | dioxane 10 ml/DMF 1% | 24 h./100° | 0 3 | 424 | 2.50 |
| 1-12 | 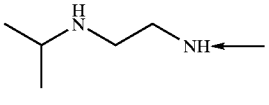 | dioxane 10 ml/DMF 1% | 24 h./100° | 0.3 | 398 | 2.46 |
| 1-13 | 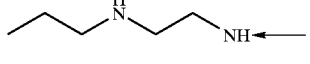 | dioxane 10 ml/DMF 1% | 24 h./100° | 0.3 | 398 | 2.48 |
| 1-14 | 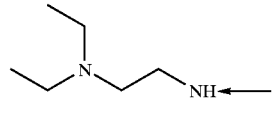 | dioxane 10 ml/DMF 1% | 24 h./100° | 0.3 | 412 | 2.47 |
| 1-15 | 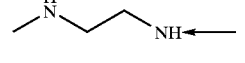 | dioxane 10 ml/DMF 1% | 24 h./100° | 0.3 | 384 | 2.48 |
| 1-16 | 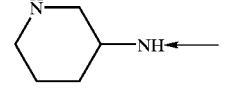 | dioxane 10 ml/DMF 1% | 24 h./100° | 0 3 | 396 | 2.49 |
| 1-17 | 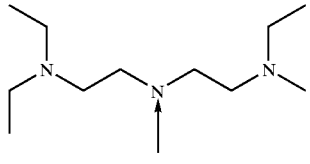 | dioxane 10 ml/DMF 1% | 24 h./100° | 0.3 | 511 | 2.38 |
| 1-18 | 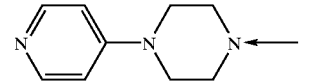 | dioxane 10 ml/DMF 1% | 24 h./100° | 0.3 | 459 | 2.62 |

-continued

| Example | Structure AlkN(R'3- | Reaction conditions | | | Characteristics | |
|---|---|---|---|---|---|---|
| | | Solvent | Heating | No. of mmol of amine | Mass MH+ | Retention time (min) |
| 1-19 | 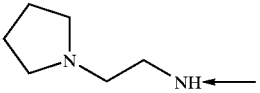 | dioxane 10 ml/DMF 1% | 24 h./100° | 0.3 | 410 | 2.44 |
| 1-20 | 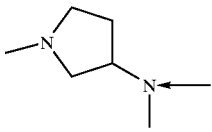 | dioxane 10 ml/DMF 1% | 24 h./100° | 0.3 | 410 | 2.52 |
| 1-21 | 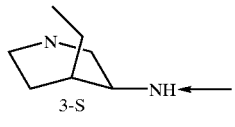 | dioxane 10 ml/DMF 1% | 24 h./100° | 0.3 | 422 | 2.55 |
| 1-22 | 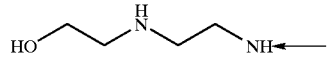 | dioxane 10 ml/DMF 1% | 24 h./100° | 0.3 | 400 | 2.36 |
| 1-23 | 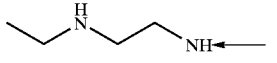 | dioxane 10 ml/DMF 1% | 24 h./100° | 0.3 | 384 | 2.40 |
| 1-24 | 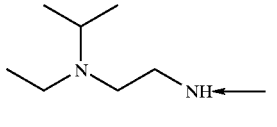 | dioxane 10 ml/DMF 1% | 24 h./100° | 0.3 | 440 | 2.58 |
| 1-25 | 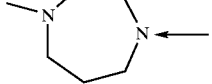 | dioxane 10 ml/DMF 1% | 24 h./100° | 0.3 | 410 | 2.48 |
| 1-26 | 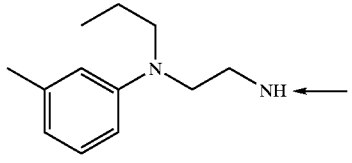 | dioxane 10 ml/DMF 1% | 24 h./100° | 0.3 | 474 | 2.86 |

EXAMPLE 2

Parallel Synthesis of Substituted Derivatives of N6-[6-amino-4-diethylamino-[1,3,5]triazin-2-yl]-2-methylquinoline-4,6-diamine

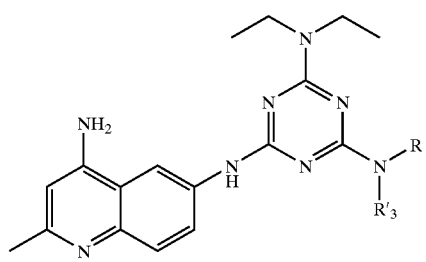

Preparation of N6-(6-chloro-4-diethylamino-[1,3,5]triazin-2-yl)-2-methylquinoline-4,6-diamine 3.91 g (22.5 mmol) of 2-methylquinoline-4,6-diamine (which may be prepared according to J. Med. Chem. 35:252, 1992), and 2.4 g (22.5 mmol) of sodium carbonate are successively added, in a 1 liter three-necked flask, to a solution of 5 g (22.5 mmol) of commercial 2,6-dichloro-4-diethylamino-[1,3,5]triazine in 300 ml of tetrahydrofuran. The reaction mixture is heated to reflux for 20 hours. After evaporation of the tetrahydrofuran, the residue is taken up in 400 ml of a mixture of water and dichloromethane (50-50 by volume). The organic phase is separated after settling out, dried over sodium sulfate and concentrated to dryness under reduced pressure. 7.4 g (92%) of N6-(6-chloro-4-diethylaminotriazin-2-yl)-2-methylquinoline-4,6-diamine are thus obtained in the form of a yellow solid whose characteristics are the following:

melting point=120° C.

$^1$H NMR spectrum (300 MHz, (CD$_3$)$_2$SO d6, δ in ppm): 1.14 (mt: 6H); 2.42 (s: 3H); from 3.50 to 3.70 (mt: 4H); 6.47

(s and unresolved complex: 3H in total); 7.54 (broad d, J=9 Hz: 1H); 7.67 (dd, J=9 and 2 Hz: 1H); 8.27 (unresolved complex: 1H); 10.09 (unresolved complex: 1H).

Parallel Synthesis of N6-[(6-(3-dimethylaminopropylamino)-4-diethylamino-[1,3,5]triazin-3-yl]-2-methylquinoline-4,6-diamine

EXAMPLE 2-1

50 mg (0.13 mmol) of N6-(6-chloro-4-diethylamino-[1,3,5]triazin-2-yl)-2-methylquinoline-4,6-diamine are introduced into a heating magnetic reactor with a Zymark condenser, of the STEM RS2050 type, containing 25 wells in parallel each provided with a 50 ml glass tube. 5 ml of DMF, 19 mg (0.14 mmol) of potassium carbonate, 21 mg (0.14 mmol) of sodium iodide and 14 mg (0.14 mmol) of 3-dimethylaminopropylamine are successively added to the first tube (Example 2-1). The reaction medium is heated at 120° C. under argon for 16 hours. After cooling, the content of the tube is evaporated under reduced pressure and taken up in 5 ml of water, filtered and washed with diethyl ether. The crude product obtained is then purified by LC/MS using a Waters Xterra 3.5 μM C18 silica column 3 mm in diameter and 50 mm in length, eluting with a linear elution gradient consisting, at the starting time ($t_0$=0 min), of water containing 0.05% trifluoroacetic acid and, at the final time ($t_f$=4 min.), of acetonitrile containing 0.05% trifluoroacetic acid. 12 mg of N6-[(6-(3-dimethyl-aminopropylamino)-4-diethylamino-[1,3,5]triazin-2-yl]-2-methylquinoline-4,6-diamine are thus obtained, after purification, whose characteristics are the following:

mass spectrum (DAD-TIC)=423 ($MH^+$)

retention time=0.79 min (the retention times are obtained on a hypersil C 18 5 μm column 50 mm diameter 4.6 mm trade mark Purity Elite, eluting with a mixture of solvents A (H2O/TFA 0.05%) and B (ACN/TFA 0.05%) with a linear gradient ranging from 95% A/5% B (t=0 min) to 10% A/90% B at t=3.5 min, then step 2 min).

Examples 2-1 to 2-2 were obtained by carrying out the procedure as above in a Zymark STEM RS2050 reactor. The structures, the various operating conditions used and the characteristics of Examples 2-1 to 2-2 are summarized in the table below:

| Example | Structure AlKN(R'3)- | Solvent | Heating | No. of mmol of amine | Mass $MH^+$ | Retention time (min) |
|---|---|---|---|---|---|---|
| 2-1 |  | DMF | 16 h./120° | 0.14 | 423 | 0.79 |
| 2-2 | 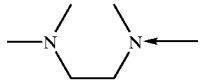 | DMF | 16 h./120° | 0.14 | 421 | 0.79 |

Table of biologica results

| Example | TRAP telomerase IC50 μM | G-4 ΔTm ° C. | Cytotoxicity A549 IC50 μM |
|---|---|---|---|
| 1-1 | 0.79 | 6 | |
| 1-2 | 0.5 | 5.6 | 7.5 |
| 1-3 | 4.4 | 3.1 | |
| 1-4 | 0.1 | 5.6 | |
| 1-5 | 1.6 | 2.8 | |
| 1-6 | 1.36 | | |
| 1-7 | 0.47 | | |
| 1-8 | 0.98 | | 8.5 |
| 1-9 | 1.64 | 7 | |
| 1-10 | 0.94 | 7 | |
| 1-11 | 1.1 | 4.5 | |
| 1-12 | 3.1 | | |
| 1-13 | 2.9 | | |
| 1-14 | 3.2 | | |
| 1-15 | 4.6 | | |
| 1-16 | 1.29 | | |
| 1-17 | 1.6 | | |
| 1-19 | 1 | | |
| 1-20 | 3.1 | | |
| 1-21 | 0.7 | | |
| 1-22 | 3.2 | | |
| 1-23 | 3.8 | | |
| 1-24 | 3.9 | | |
| 1-25 | 1.5 | | 10 |
| 1-26 | 0.86 | 33 | <0.3 |
| 2-1 | 0.90 | 7.9 | |
| 2-2 | 5.4 | 2.4 | |

We claim:

1. A compound which binds the G-quadruplex structure of a telomere comprising the following general formula:

nitrogen-containing aromatic ring —NR$_3$— distribution agent —NR'$_3$— nonaromatic hydrocarbon chain in which 1) the nitrogen-containing aromatic ring represents:
   a) a quinoline optionally substituted with at least
      i) a group N(Ra)(Rb) in which Ra and Rb, which are identical or different, represent hydrogen or a C1–C4 alkyl radical or
      ii) a group ORa in which Ra is as defined above
   b) a quinoline possessing a nitrogen atom in quaternary form
   c) a benzamidine or
   d) a pyridine, attached at the 4-position, 2) R$_3$ and R'$_3$, which are identical or different, represent independently of each other, hydrogen or a C1–C4 alkyl radical, 3) the distribution agent represents:
   a triazine group, a triazine group substituted with (i) an alkyl radical having 1 to 4 carbon atoms, (ii) a thio radical, (iii) an hydroxy radical, or (iv) an amino radical, wherein the thiol, hydroxy or amino radicals are unsubstituted or substituted with
   one or more short-chain alkyl groups containing 1 to 4 carbon atoms and wherein the alkyl is unsubstituted or substituted with a halogen atom or
   or a salt thereof.

2. The compound according to claim 1, wherein the distribution agent is a triazine group.

3. The compound according to claim 1, wherein the nonaromatic hydrocarbon chain is chosen from among
   i) alkyl (C1–C4), alkenyl (C2–C4), wherein the alkyl and alkenyl are linear or branched,
   ii) cycloalkyl (C3–C18)
   iii) cycloalkenyl (C3–C18)
   iv) heterocycloalkyl (C3–C18) and
   v) heterocycloalkyl (C3–C18) including the nitrogen atom of the NR'$_3$ group.

4. The compounds according to claim 3, wherein the nonaromatic hydrocarbon chain is unsubstituted or substituted with one or more atoms or radicals chosen from among halogen atoms, hydroxyl, aryl, heteroaryl, alkyloxy, aryloxy, thiol, alkylthio, arylthio, amino, alkylamino, arylamino, dialkylamino, diarylamino, amidino, guanidino, alkylcarbonylamino, arylcarbonylamino, carboxyl, alkyloxycarbonyl, aryloxycarbonyl, aminocarbonyl, alkylaminocarbonyl, arylaminocarbonyl, dialkylaminocarbonyl, alkylcarbonyl, arylcarbonyl, cyano, trifluoromethyl, and combinations thereof.

5. The compounds according to claim 4, wherein the alkyl chains comprise substituents having a hydrocarbon chain containing 1 to 4 carbon atoms, and the aryl groups comprise substituents having a hydrocarbon chain containing 5 to 18 carbon atoms.

6. The compounds according to claim 3, wherein the alkyl chains contain 2 to 3 carbon atoms, and the heterocycloalkyl or cycloalkyl chains contain 5 to 7 carbon atoms.

7. The compounds according to claim 1, comprising formula (I) below:

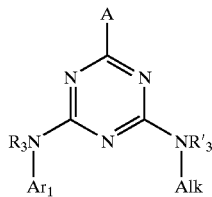

in which:
1) A represents:
   a) an amino group of formula NR1R2 in which R1 and R2, which are identical or different, represent hydrogen or a straight or branched alkyl group containing 1 to 4 carbon atoms or
   b) a group OR1 or SR1 in which R1 has the same meaning as above or
   c) an alkyl group containing 1 to 4 carbon atoms or a trifluoromethyl group or
   d) a hydrogen atom or
   e) a halogen atom chosen from fluorine, chlorine, bromine and iodine,
2) $R_3$ and $R'_3$, which are identical or different, represent independently of each other hydrogen or a C1–C4 alkyl group,
3) $Ar_1$ represents a nitrogen-containing aromatic ring representing:
   a) a quinoline, either unsubstituted or substituted with at least
      i) a group N(Ra)(Rb) in which Ra and Rb, which are identical or different, represent hydrogen or a C1–C4 alkyl radical or
      ii) a group ORa in which Ra is as defined above
   b) a quinoline possessing a nitrogen atom in quaternary for
   c) a benzamidine or
   d) a pyridine attached at the 4-position or fused with an aryl or heteroaryl group
   e) a pyridine attached at the 4-position or fused with an aryl or heteroaryl group substituted with a C1–C4 alkyl group,
4) Alk represents a nonaromatic unsubstituted or substituted hydrocarbon chain chosen from among alkyl (C1–C4), alkenyl (C2–C4), wherein the alkyl and alkenyl chain are linear or branched, cycloalkyl (C3–C18), cycloalkenyl (C3–C18) heterocycloalkyl (C3–C18), and heterocycloalkyl (C3–C18) including the nitrogen atom of the NR'3 group.

or a salt thereof.

8. The compound according to claim 7, wherein the nonaromatic hydrocarbon chain is unsubstituted or substituted with one or more atoms or radicals chosen from among halogen atoms, hydroxyl, aryl, heteroaryl, alkyloxy, aryloxy, thiol, alkylthio, arylthio, amino, alkylamino, arylamino, dialkylamino, diarylamino, amidino, guanidino, alkylcarbonylamino, arylcarbonylamino, carboxyl, alkyloxycarbonyl, aryloxycarbonyl, aminocarbonyl, alkylaminocarbonyl, arylaminocarbonyl, dialkylaminocarbonyl, alkylcarbonyl or arylcarbonyl, cyano, trifluoromethyl, and combinations thereof.

9. The compounds according to claim 7, wherein $Ar_1$ represents 4-amino- or 4-methylamino- or 4-dimethylamino-quinolyl or quinolinium, wherein the quinolinium nucleus is unsubstituted or substituted with a methyl group.

10. The compounds according to claim 7, wherein group A represents a thiomethyl, amino, alkylamino or dialkylamino, in which the alkyl groups in the radicals possess 1 to 4 carbon atoms.

11. The compounds according to claim 7, wherein A represents a methylthio group.

12. The compounds according to claim 7, wherein Alk represents an alkyl containing 2 to 3 linear or branched carbon atoms, wherein the alkyl is substituted with
   i) an amino, alkylamino, arylamino, dialkylamino, diarylamino, or combination thereof
   ii) an alkenyl unit containing 2 to 3 carbon atoms, which is substituted with an amino, alkylamino arylamino, dialkylamino, diarylamino, heterocyclyl containing from 4 to 7 carbon atoms, or a combination thereof.

13. The compounds according to claim 7, wherein Alk represents a 2-(dialkylamino)ethyl, 3-(dialkylamino)propyl, 2-(N-alkyl-N-arylamino)ethyl, or 3-(N-alkyl-N-arylamino) propyl, in which the alkyl groups contain 1 to 4 carbon atoms and the aryl groups contain 5 to 18 carbon atoms.

14. The compounds according to claim 7, wherein Alk represents 2-(N-m-tolyl-N-ethylamino)ethyl.

15. A compounds corresponding to the following formula (I):

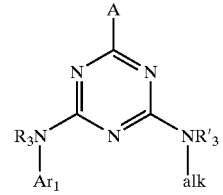

in which:
1) A represents
   a) an amino group of formula NR1R2 in which R1 and R2, which are identical or different, represent hydrogen or a straight or branched alkyl group containing 1 to 4 carbon atoms or
   b) a group OR1 or SR1 in which R1 has the same meaning as above
   c) an alkyl group containing 1 to 4 carbon atoms or a trifluoromethyl group
   d) a hydrogen atom or
   e) a halogen atom chosen from fluorine, chlorine, bromine and iodine,
2) $R_3$ and $R'_3$, which are identical or different, represent independently of each other hydrogen or a C1–C4 alkyl group,
3) $Ar_1$ represents a nitrogen-containing aromatic ring representing:
   a) a quinoline, either unsubstituted or substituted with at least
      i) a group N(Ra)(Rb) in which Ra and Rb, which are identical or different, represent hydrogen or a C1–C4 alkyl radical or
      ii) a group ORa in which Ra is as defined above
   b) a quinoline possessing a nitrogen atom in quaternary form or c) a benzamidine or d) a pyridine attached at the 4-position or fused with an aryl or heteroaryl group or e) a pyridine attached at the 4-position or fused with an aryl or heteroaryl group substituted with a C1–C4 alkyl group, 4) alk represents a nonaromatic unsubstituted or substituted hydrocarbon chain chosen from among alkyl (C1–C4), alkenyl (C2–C4), wherein the alkyl and alkenyl chain are linear or branched, cycloalkyl (C3–C18), cycloalkenyl (C3–C18), heterocycloalkyl (C3–C18), and heterocycloalkyl (C3–C18) including the nitrogen atom of the NR'3 group, or a salt thereof.

16. The compounds according to claim 15, wherein the nonaromatic hydrocarbon chain is unsubstituted or substituted with one or more atoms or radicals chosen from among halogen atoms, hydroxyl, aryl, heteroaryl, alkyloxy, aryloxy, thiol, alkylthio, arylthio, amino, alkylamino, arylamino, dialkylamino, diarylamino, amidino, guanidino, alkylcarbonylamino, arylcarbonylamino, carboxyl, alkyloxycarbonyl, aryloxycarbonyl, aminocarbonyl, alkylaminocarbonyl, arylaminocarbonyl, dialkylaminocarbonyl, alkylcarbonyl, arylcarbonyl, cyano, trifluoromethyl, and combinations thereof.

17. The compounds according to claim 15, wherein $Ar_1$ represents 4-amino- or 4-methylamino- or 4-dimethylamino-quinolyl or quinolinium, wherein the quinolinium nucleus is unsubstituted or substituted with a methyl group.

18. The compounds according to claim 15, wherein group A represents a thiomethyl, amino, alkylamino or dialkylamino, in which the alkyl groups in the radicals possess 1 to 4 carbon atoms.

19. The compounds according to claim 15, wherein R1 and R2 represent hydrogen.

20. The compound according to claim 18, wherein A represents a methylthio group.

21. The compound according to claim 15, wherein alk represents i) an alkyl containing 2 to 3 linear or branched carbon atoms which is substituted with an amino, alkylamino, arylamino, dialkylamino, diarylamino, or combination thereof, ii) an alkenyl unit containing 2 to 3 carbon atoms, which is substituted with an amino, alkylamino, arylamino, dialkylamino, diarylamino, or combination thereof, or iii) a heterocyclyl containing from 4 to 7 carbon atoms.

22. The compound according to claim 15, wherein alk represents 2-(dialkylamino)ethyl, 3-(dialkylamino)propyl, 2-(N-alkyl-N-arylamino)ethyl or 3-(N-alkyl-N-arylamino) propyl, in which the alkyl groups contain 1 to 4 carbon atoms and the aryl groups contain 5 to 18 carbon atoms.

23. The compound according to claim 21, characterized in that alk represents a 2-(N-m-tolyl-N-ethylamino)ethyl.

24. A therapeutic composition comprising a compound according to claim 1 and one or more anticancer compounds.

25. The composition according to claim 24, wherein the one or more anticancer compounds are chosen from among alkylating agents, platinum derivatives, antibiotic agents, antimicrotubule agents, anthracyclines, group I and II topoisomerases, fluoropyrimidines, cytidine analogs, adenosine analogs, L-asparaginase, hydroxyurea, transretinoic acid, suramine, irinotecan, topotecan, dexrazoxane, amifostine, herceptin, estrogenic hormones, and androgenic hormones.

26. A method of using the composition of claim 25, wherein the individual compounds are administered in a therapeutically effective amount to a patient simultaneously separately or sequentially.

27. A method of inhibiting telomerase activity, comprising administering a therapeutically effective amount of one or more compounds of claim 1 to a patient, wherein the level of telomerase activity in the patient following the administration is reduced relative to the level of telomerase activity existing prior to the administration.

28. A method of treating a cancer, comprising administering a therapeutically effective amount of one or more compounds of claim 1 to a patient in need of such a treatment, wherein the level of telomerase activity following the administration is reduced relative to the level of telomerase activity existing prior to the administration.

29. A pharmaceutical composition comprising one or more compounds of claim 1, and a pharmaceutically acceptable carrier.

30. A therapeutic combination consisting of the administration of one or more compounds according to claim 1 and the administration of radiation.

* * * * *

SEQUENCE LISTING

<160> NUMBER OF SEQ ID NOS: 3

<210> SEQ ID NO 1
<211> LENGTH: 21
<212> TYPE: DNA
<213> ORGANISM: Artificial sequence
<220> FEATURE:
<223> OTHER INFORMATION: oligonucleotide probe

<400> SEQUENCE: 1
gggttagggt tagggttagg g                                    21

<210> SEQ ID NO 2
<211> LENGTH: 18
<212> TYPE: DNA
<213> ORGANISM: Artificial sequence
<220> FEATURE:
<223> OTHER INFORMATION: oligonucleotide probe

<400> SEQUENCE: 2
aatcgttcga gcagagtt                                        18

<210> SEQ ID NO 3
<211> LENGTH: 27
<212> TYPE: DNA
<213> ORGANISM: Artificial sequence
<220> FEATURE:
<223> OTHER INFORMATION: oligonucleotide probe

<400> SEQUENCE: 3
gtgcccttac ccttaccctt accctaa                              27